(12) United States Patent
Kusumi et al.

(10) Patent No.: US 10,565,687 B2
(45) Date of Patent: Feb. 18, 2020

(54) IMAGE PROCESSING APPARATUS, IMAGING APPARATUS, IMAGE PROCESSING METHOD, IMAGE PROCESSING PROGRAM, AND RECORDING MEDIUM

(71) Applicant: CANON KABUSHIKI KAISHA, Tokyo (JP)

(72) Inventors: Yuichi Kusumi, Utsunomiya (JP); Chiaki Inoue, Utsunomiya (JP); Yoshiaki Ida, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 86 days.

(21) Appl. No.: 15/824,975

(22) Filed: Nov. 28, 2017

(65) Prior Publication Data

US 2018/0150941 A1 May 31, 2018

(30) Foreign Application Priority Data

Nov. 30, 2016 (WO) .................. PCT/JP2016/085511

(51) Int. Cl.
*G01N 21/55* (2014.01)
*G06T 5/00* (2006.01)
(Continued)

(52) U.S. Cl.
CPC ............. *G06T 5/002* (2013.01); *G01N 21/55* (2013.01); *G06T 5/50* (2013.01); *G06T 7/90* (2017.01);
(Continued)

(58) Field of Classification Search
CPC combination set(s) only.
See application file for complete search history.

(56) References Cited

U.S. PATENT DOCUMENTS 8,488,879 B2 * 7/2013 Kobiki ...................... G06T 7/11
382/165
9,489,728 B2 * 11/2016 Imagawa ................ G06T 5/005
(Continued)

FOREIGN PATENT DOCUMENTS

JP 2008-099149 A 4/2008
JP 2013-65215 A 4/2013
(Continued)

OTHER PUBLICATIONS

Hisashi Kobiki, et al., "Specular Reflection Control Technology to Increase Glossiness of Images", Sep. 1, 2013, vol. 68, No. 9, pp. 38-41, No. 2013-00097-009 (Partial translation of Company Technological Report 2013-00097-009).
(Continued)

*Primary Examiner* — Tsung Yin Tsai
(74) *Attorney, Agent, or Firm* — Canon U.S.A., Inc. I.P. Division (57) ABSTRACT

One or more image processing apparatuses, imaging apparatuses, image processing methods, image processing programs, and recording mediums are provided herein. At least one image processing apparatus includes a hue obtaining unit configured to perform a noise reduction process on an input image or a first hue of the input image so as to obtain a second hue having reduced noise, an extraction unit configured to extract a plurality of pixels from the input image based on the second hue having the reduced noise, and an estimation unit configured to estimate diffuse reflection components based on the plurality of extracted pixels.

15 Claims, 7 Drawing Sheets

(51) Int. Cl.
*G06T 7/90* (2017.01)
*G06T 5/50* (2006.01)
*G01N 21/47* (2006.01)

(52) U.S. Cl.
CPC .............. *G01N 21/4738* (2013.01); *G06T 2207/20224* (2013.01)

(56) References Cited

U.S. PATENT DOCUMENTS

| | | | |
|---|---|---|---|
| 2009/0195686 A1* | 8/2009 | Shintani | H04N 5/232 348/333.11 |
| 2013/0071018 A1* | 3/2013 | Kobiki | G06K 9/4661 382/165 |
| 2014/0126835 A1* | 5/2014 | Shioya | G06T 5/008 382/274 |
| 2015/0235375 A1* | 8/2015 | Imagawa | G06T 5/005 382/164 |
| 2016/0163066 A1 | 6/2016 | Ishihara | |

FOREIGN PATENT DOCUMENTS

| | | |
|---|---|---|
| JP | 2014-137691 A | 7/2014 |
| JP | 2015-023403 A | 2/2015 |

OTHER PUBLICATIONS

Tomoaki Higo, et al., "Realtime Removal of Specular Reflection Component Based on Dichromatic Reflection Model", Technical Report on Computer Vision and Image Media, pp. 211 to 218, Sep. 2006 (includes English abstract).

Hisashi Kobiki, et al., "Specular Reflection Control Technology to Increase Glossiness of Images", Sep. 1, 2013, vol. 68, No. 9, pp. 38-41 (includes English abstract).

International Search Report and Written Opinion for PCT/JP2016/085511 and notification of transmittal of the ISR/WO, dated Dec. 27, 2016 (English translation of International Search Report included herewith).

* cited by examiner

IMAGE PROCESSING APPARATUS, IMAGING APPARATUS, IMAGE PROCESSING METHOD, IMAGE PROCESSING PROGRAM, AND RECORDING MEDIUM

TECHNICAL FIELD

The present disclosure relates to one or more embodiments of an image processing apparatus, an imaging apparatus, an image processing method, an image processing program, and a recording medium.

BACKGROUND ART

As image processing after imaging, various images may be generated by separating diffuse reflection components from specular reflection components in an input image. For example, an image in which gloss is controlled may be generated by using diffuse reflection components and specular reflection components serving as gloss components which are separated from each other.

Furthermore, a surface normal required for generation of an image while lighting to an object is changed may be obtained with high accuracy. A view of an object is determined in accordance with information on a shape of the object, information on reflectance of the object, information on a light source, and the like. A physical behavior of reflection light obtained by reflecting light emitted from a light source by an object depends on a local surface normal, and therefore, in particular, a surface normal of the object is effectively used as the shape information instead of a 3D shape. As a method for obtaining a surface normal of an object, a photometric stereo method is used. In the photometric stereo method, a surface normal is obtained on the assumption that an object performs Lambertian diffuse reflection, and therefore, only diffuse reflection components of an input image are required. Therefore, a technique of estimating diffuse reflection components in an image is required. If diffuse reflection components in an image may be estimated, specular reflection components may be simultaneously obtained by subtracting the diffuse reflection components from the image.

PTL 1 and NPL 1 disclose a method for estimating diffusion reflection components in an input image based on pixels extracted for individual hues of the input image utilizing a fact that an object obeys a dichromatic reflection model. In the dichromatic reflection model, reflection light from an object may be represented by a linear sum of diffuse reflection components serving as an object color and specular reflection components serving as a light source color.

In this method, pixels are extracted for individual hues of an input image so that diffuse reflection components are estimated for individual objects having the same diffuse reflectance. When the light source emits white light, a hue of an object depends on only the diffuse reflection components serving as an object color and does not relates to presence or absence of the specular reflection components serving as a light source color, and therefore, pixels may be extracted only from objects having the same diffuse reflectance using hue.

CITATION LIST

Patent Literature

PTL 1 Japanese Patent Laid-Open No. 2013-65215

Non Patent Literature

NPL 1 Tomoaki HIGO, Daisuke MIYAZAKI, Katushi IKEUCHI, "Realtime Removal of Specular Reflection Component Based on Dichromatic Reflection Model", Technical Report on Computer Vision and Image Media, pp. 211 to 218, 2006

However, if an input image includes noise, accuracy of extraction of pixels is degraded due to variation in hue of the input image, and consequently, accuracy of estimation of diffuse reflection components is also degraded.

PTL 1 discloses a method for suppressing degradation of extraction accuracy by controlling a hue range when pixels are extracted relative to the variation in hue of the input image caused by noise. Specifically, the hue range of pixels to be extracted is increased when noise is large.

However, if the hue range of extraction is increased, pixels may be extracted from other objects having similar hue. Since the diffuse reflection components are estimated on the assumption that pixels extracted for individual hues are included in objects having the same diffusion reflectance, if pixels of objects having different diffusion reflectances are extracted in a mixed manner, accuracy of the estimation of the diffuse reflection components is degraded.

SUMMARY OF INVENTION

To address the above issue(s), one or more embodiments of the present disclosure provide an image processing apparatus, an imaging apparatus, an image processing method, an image processing program, and a recording medium which may estimate diffuse reflection components in an input image with high accuracy by reducing influence of noise.

According to one or more embodiments of the present disclosure, an image processing apparatus includes a hue obtaining unit configured to perform a noise reduction process on an input image or a first hue of the input image so as to obtain a second hue having reduced noise, an extraction unit configured to extract a plurality of pixels from the input image based on the second hue having the reduced noise, and an estimation unit configured to estimate diffuse reflection components based on the plurality of extracted pixels.

According to one or more further embodiments of the present disclosure, an imaging apparatus includes an imaging element configured to capture an image of an object, and an image processor configured to perform a noise reduction process on an input image or a first hue of the input image so as to obtain a second hue having reduced noise, extract a plurality of pixels from the input image based on the second hue having the reduced noise, and estimate diffuse reflection components based on the plurality of extracted pixels.

According to one or more additional embodiments of the present disclosure, an image processing method includes obtaining a second hue having reduced noise by performing a noise reduction process on an input image or a first hue of the input image, and extracting a plurality of pixels from the input image based on the second hue having the reduced noise and estimating diffuse reflection components based on the plurality of extracted pixels.

Further features of the present disclosure will become apparent from the following description of exemplary embodiments with reference to the attached drawings.

DESCRIPTION OF EMBODIMENTS

Hereinafter, embodiments of the present disclosure will be described in detail with reference to the accompanying drawings. In the drawings, the same components are denoted by the same reference numerals and redundant descriptions are omitted.

First Embodiment

A first embodiment of the present disclosure will be described in detail hereinafter.

An imaging apparatus of this embodiment estimates diffuse reflection components in an input image.

Figure 1:
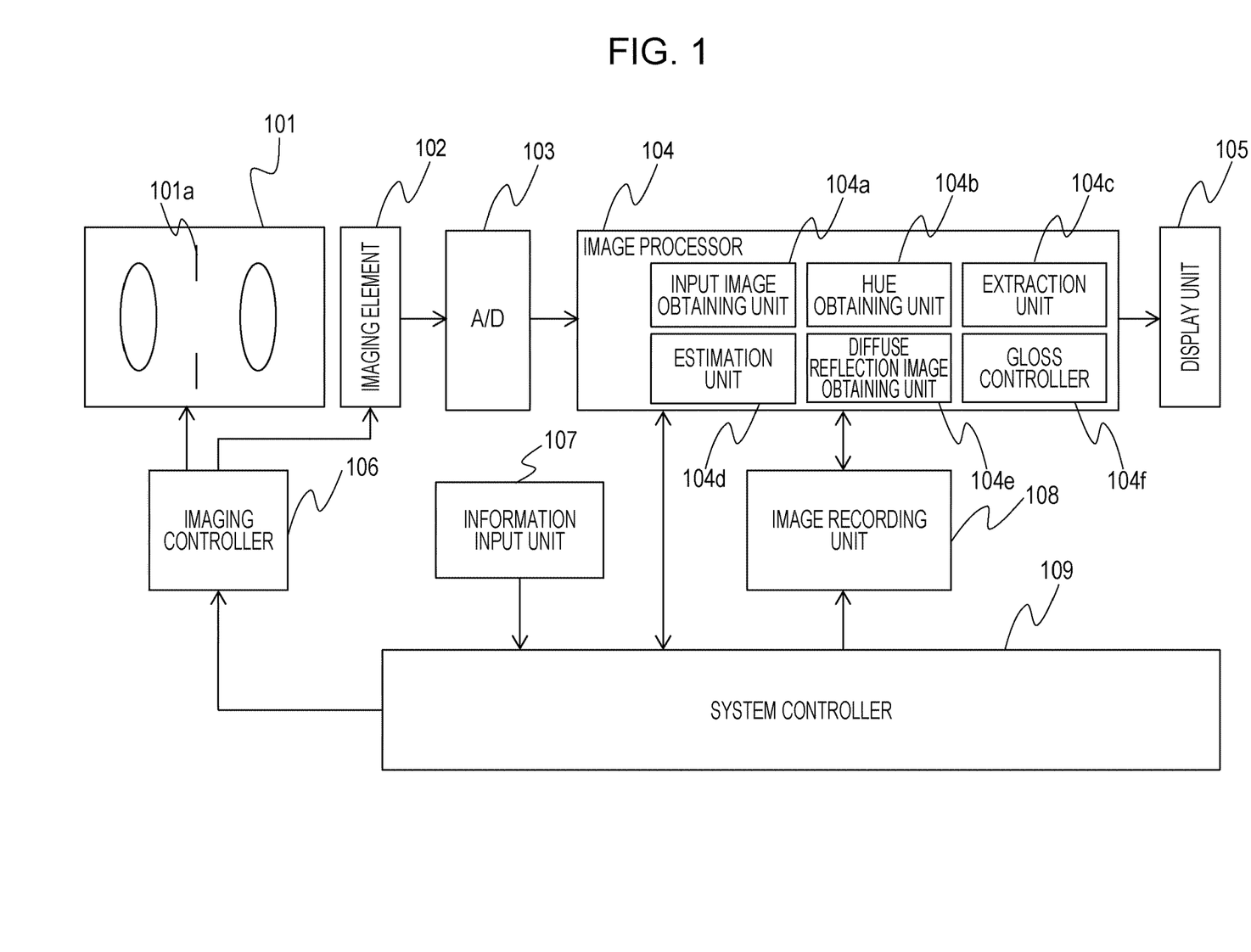
FIG. 1 is a block diagram illustrating an imaging apparatus according to first and second embodiments.

FIG. 1 is a block diagram illustrating the imaging apparatus. An imaging optical system 101 includes a diaphragm 101a which forms an image on an imaging element 102 using light emitted from an object. The imaging element 102 includes a photoelectric conversion element, such as a CCD sensor or a CMOS sensor, and captures an image of the object. An analog electric signal generated by photoelectric conversion performed by the imaging element 102 is converted into a digital signal by an A/D converter 103 and supplied to an image processor 104. Note that the imaging optical system 101 may be incorporated in an imaging apparatus 100 or may be detachably attached to the imaging apparatus 100 similarly to a single-lens reflex camera.

The image processor 104 estimates diffuse reflection components in the input image while performing general image processing on the digital signal. The image processor 104 includes an input image obtaining unit 104a, a hue obtaining unit 104b which obtains hue having reduced noise (a second hue), an extraction unit 104c which extracts pixels for individual hues, and an estimation unit 104d which estimates diffuse reflection components from the extracted pixels. The image processor 104 further includes a diffuse reflection image obtaining unit (image generation unit) 104e which obtains (generates) a diffuse reflection image based on the estimated diffuse reflection components and a gloss controller 104f which performs gloss control on an image based on the diffuse reflection image and the specular reflection image.

An output image processed by the image processor 104 is stored in an image recording unit 108, such as a semiconductor memory or an optical disc. The output image may be displayed in a display unit 105.

In this embodiment, the input image obtaining unit 104a, the hue obtaining unit 104b, the extraction unit 104c, the estimation unit 104d, the diffuse reflection image obtaining unit (image generation unit) 104e, and the gloss controller 104f are incorporated in the imaging apparatus. However, an image processing apparatus incorporating these units may be provided separately from the imaging apparatus.

An information input unit 107 supplies imaging conditions (including an aperture value, an exposure time, and a focal length) selected by a user to a system controller 109. An imaging controller 106 obtains an image under the desired imaging conditions selected by the user based on information supplied from the system controller 109.

Figure 2:
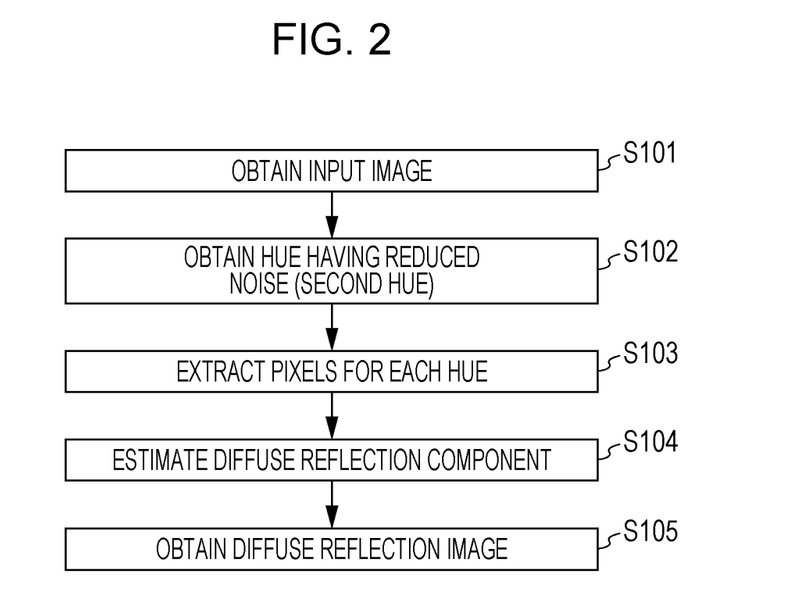
FIG. 2 is a flowchart of an image processing method according to the first embodiment.
Figure 3:
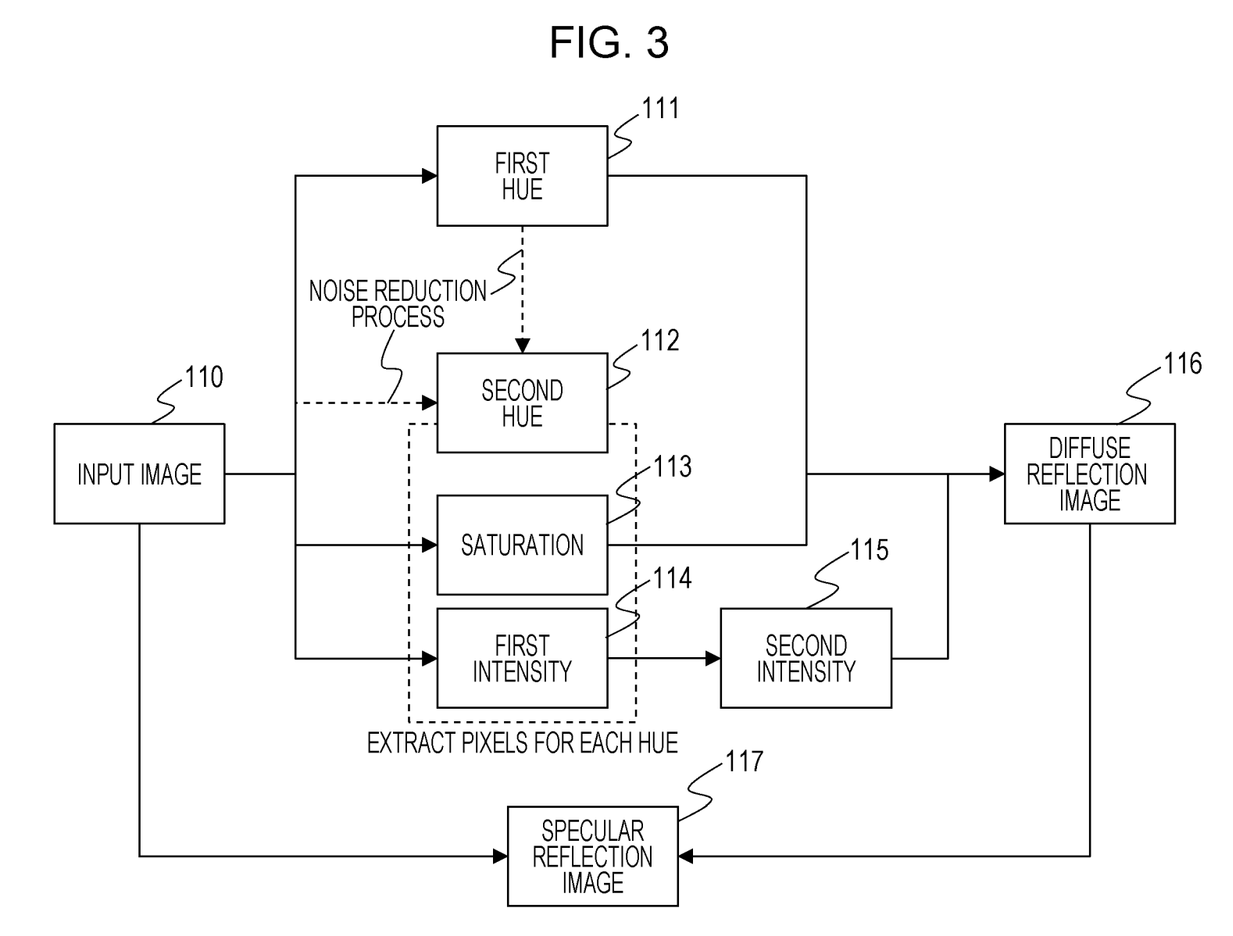
FIG. 3 is a diagram schematically illustrating a flow of obtainment of a diffuse reflection image from an input image.

FIG. 2 is a flowchart of an image processing method according to this embodiment, and FIG. 3 is a diagram schematically illustrating a flow of obtainment (generation) of a diffuse reflection image from an input image. The image processing method of this embodiment is executed in accordance with an image processing program serving as a computer program by the system controller 109 and the image processor 104. Note that the image processing program may be recorded in a computer-readable recording medium, for example.

In step S101, the input image obtaining unit 104a obtains a captured image as an input image 110 from the imaging apparatus 100. The input image obtaining unit 104a may obtain an image obtained by performing a noise reduction process on the captured image as the input image. In a case where the image processor 104 is configured as an image processing apparatus separately from the imaging apparatus, the input image 110 may be obtained by communication between the imaging apparatus and the image processing apparatus in a wired manner or a wireless manner or may be obtained through a storage medium, such as a semiconductor memory or an optical disc.

In step S102, the hue obtaining unit 104b obtains hue having reduced noise (a second hue 112). As described above, when noise is included in the input image 110, accuracy of extraction of pixels described below is degraded due to variation in hue, and as a result, accuracy of estimation of diffuse reflection components is also degraded. Accordingly, the obtainment and the use of the hue having reduced noise reduce influence of noise.

For example, the second hue 112 in the image obtained by performing the noise reduction process on the input image 110 is obtained. Alternatively, the second hue 112 may be obtained by performing the noise reduction process on a hue (a first hue 111) of the input image 110.

When the light source emit white light, the hue 111 of the input image 110 only depends on the diffuse reflection components and does not relate to the specular reflection components. Therefore, in step S103 described below, by using the first hue 111, pixels may be extracted only from objects having the same diffuse reflectance. Accordingly, it is preferable that white balance correction is performed on the captured image or the input image 110 in advance so that an image under a white light source is obtained.

A hue is calculated based on Expressions (1) and (2) below. Here, "r", "g", and "b" correspond to R, G, and B values in an image from which the hue is calculated.

$$\begin{pmatrix} I_x \\ I_y \\ I_z \end{pmatrix} = \begin{pmatrix} 1 & -\frac{1}{2} & -\frac{1}{2} \\ 0 & \frac{\sqrt{3}}{2} & -\frac{\sqrt{3}}{2} \\ \frac{1}{3} & \frac{1}{3} & \frac{1}{3} \end{pmatrix} \begin{pmatrix} r \\ g \\ b \end{pmatrix} \quad (1)$$

$$\text{hue} = \arctan\frac{I_x}{I_y} \quad (2)$$

Specifically, the hue is calculated in accordance with Expression (3) below based on Expressions (1) and (2).

$$\text{hue} = \arctan\left(\frac{\frac{\sqrt{3}}{2}g - \frac{\sqrt{3}}{2}b}{r - \frac{1}{2}g - \frac{1}{2}b}\right) \quad (3)$$

The noise reduction process may be performed by any one of various general methods. More specifically, a method which enables reduction of noise while edges are stored is preferably employed. Examples of such an edge storage noise reduction method include a bilateral filter, a non local means (NLM) filter, and a guided filter. Alternatively, the noise reduction process may be performed using a plurality of images.

Since the variation in hue is changed depending on a noise amount of the input image 110, the noise reduction process is preferably performed based on the noise amount of the input image 110. As the noise amount of the input image 110 becomes larger, the variation in hue also becomes larger, and therefore, a degree of the noise reduction process is increased. The noise amount of the input image 110 may be determined based on an ISO speed and a luminance value at a time of imaging. Alternatively, the noise amount may be estimated from the input image 110.

Furthermore, the variation in hue caused by the noise is changed in accordance with brightness of color in the input image 110, and therefore, the noise reduction process may be performed based on the brightness of the color in the input image 110. As differences among R, G, and B values in a region of an image become smaller, that is, as brightness of color in a region becomes lower, the variation in hue becomes larger, and therefore, the degree of the noise reduction process is increased. As color brightness, saturation in a color space, such as HLS or HSV, may be used or differences among R, G, and B values may be used. Furthermore, saturation represented by Expression (4) below may be used.

In step S103, the extraction unit 104c extracts pixels from the input image 110 based on the second hue 112 obtained in step S102.

In NPL 1, pixels are extracted from the input image 110 based on the first hue 111 in this embodiment. However, the first hue 111 has variation due to influence of noise as described above. Therefore, accuracy of the extraction of pixels from the input image 110 is lowered. Since pixels are extracted based on the second hue 112 having the reduced noise in this embodiment, pixels may be extracted with high accuracy. Although pixels are extracted for individual hues from the input image 110 based on the second hue 112 in this step, a range of hue of pixels to be extracted may be set.

Next, in step S104, the estimation unit 104d estimates diffuse reflection components in the input image 110 based on the pixels extracted for individual hues in step S103.

Figure 4:
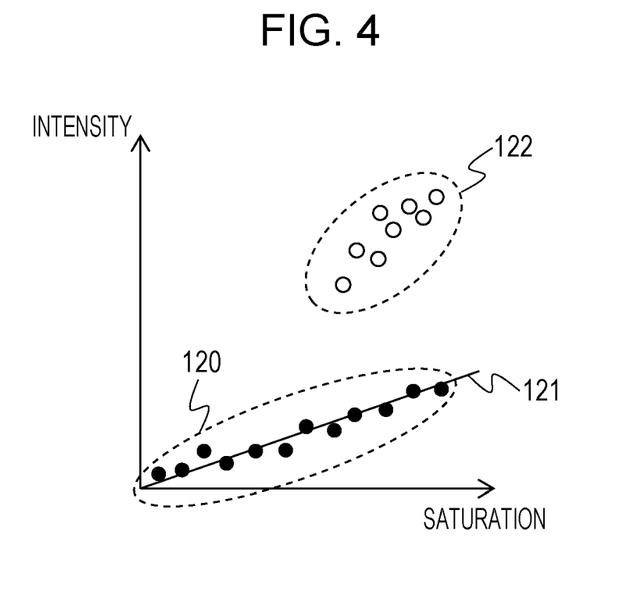
FIG. 4 is a diagram illustrating diffuse reflection components and specular reflection components in a saturation-intensity plane.

As illustrated in FIG. 4, when pixels extracted for individual hues are plotted in a plane of saturation and intensity calculated in accordance with Expressions (4) and (5), respectively, diffuse reflection components 120 exist on a straight line 121 which passes an origin. Furthermore, when a light source emits white light, saturation of components 122 obtained by adding specular reflection to diffuse reflection components is not changed but only intensity is changed.

$$\text{saturation} = \sqrt{I_x^2 + I_y^2} \quad (4)$$

$$\text{intensity} = I_z^2 \quad (5)$$

Therefore, saturation 113 and intensity (a first intensity 114) of pixels extracted for individual hues in step S103 are obtained and an inclination of the straight line 121 including the input image 110 is estimated.

The inclination of the straight line 121 is estimated using one of various fitting methods. When the inclination of the straight line 121 is to be estimated, only the diffuse reflection components 120 are required. However, the components 122 obtained by adding the specular reflection are unrequired outliers, and therefore, a fitting method which avoids the outliers is preferably employed. To except the components 122 obtained by adding the specular reflection, the inclination of the straight line 121 may be estimated only from the pixels having the smallest first intensity 114 in the individual saturation levels.

Figure 5:
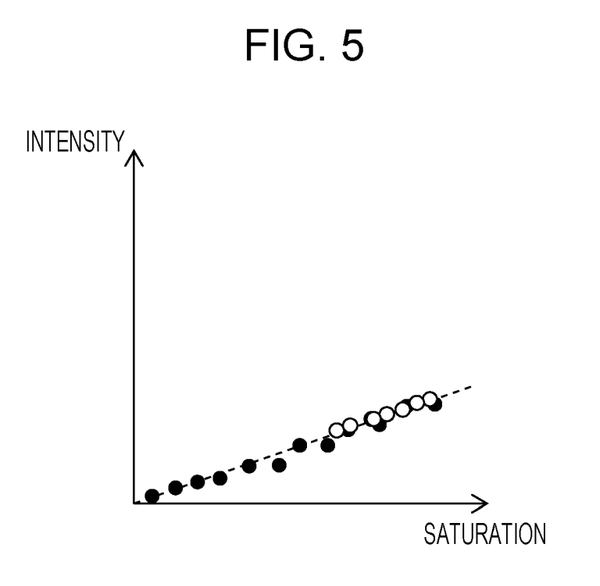
FIG. 5 is a diagram illustrating estimation of the diffuse reflection components.

Pixels having the first intensity 114 which is larger than intensity of the straight line 121 obtained from the estimated inclination, that is, intensity (diffuse reflection intensity) of the diffuse reflection components 120 may be determined as the components 122 obtained by adding the specular reflection. When the first intensity 114 in such pixels are replaced by the second intensity 115 so that the straight line 121 is obtained as illustrated in FIG. 5, the diffuse reflection components are obtained by removing the specular reflection components. Alternatively, the first intensity 114 in all the extracted pixels may be replaced by the second intensity 115 which is diffuse reflection intensity represented by the straight line 121.

The estimated inclination of the straight line 121 is a parameter determined by diffusion reflectance of the object, and different parameters are obtained in different objects. Therefore, diffuse reflection components may be obtained for each object classified according to hue by obtaining the inclination of the straight line 121 by extracting pixels for each hue of the object.

Furthermore, only when the light source emits white light, saturation of the components 122 obtained by adding the specular reflection is not changed but only intensity is changed relative to the diffuse reflection components 120. Therefore, white balance connection is preferably performed on the input image 110 in advance so that an image under a white light source is obtained.

Next, in step S105, the diffuse reflection image obtaining unit (image generation unit) 104e obtains (generates) a diffuse reflection image 116 based on the second intensity 115 of the diffuse reflection components obtained in step S104, the saturation 113, and the hue. Here, the hue corresponds to the first hue 111 of the extracted pixels. Alternatively, the second hue 112 obtained in step S102 may be used. The diffuse reflection image 116 may be obtained by performing inverse transform on Expressions (1) to (5) described above.

Figure 6:
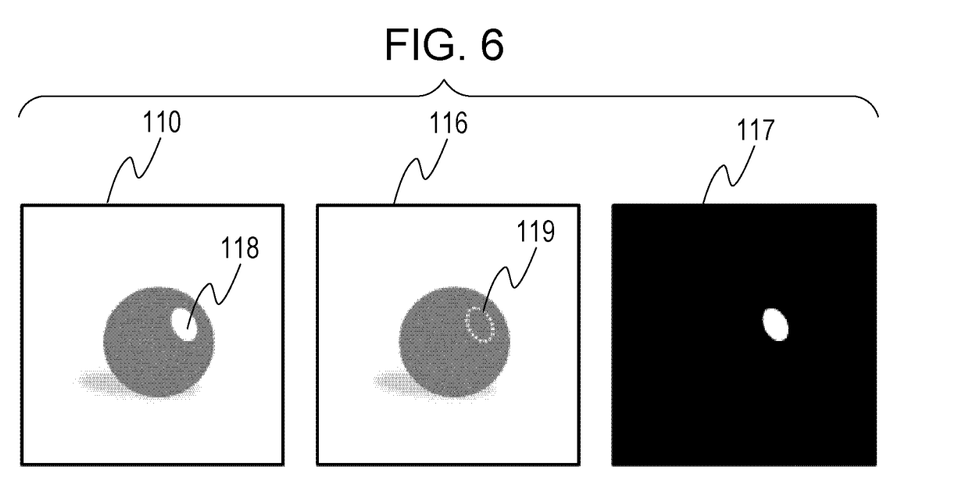
FIG. 6 is a diagram illustrating the input image, the diffuse reflection image, and the specular reflection image.

Furthermore, a specular reflection image 117 may be obtained (generated) using the obtained diffuse reflection image 116 and the input image 110. Specifically, as illustrated in FIG. 6, the specular reflection image 117 may be obtained (generated) by subtracting the diffuse reflection image 116 from the input image 110. Here, a reference numeral 118 denotes a specular reflection region 118 in the input image 110 in FIG. 6, and a reference numeral 119 denotes a region in the diffuse reflection image 116 from which the specular reflection components are removed from the input image 110.

Furthermore, the gloss controller 104f may obtain (generate) an image in which gloss is controlled using the obtained diffuse reflection image 116 and the specular reflection image 117 or the input image 110. Since the gloss of the image is based on the specular reflection components, an image in which gloss is controlled may be obtained by weighting addition which changes a rate of the specular reflection image 117 to be added to the obtained diffuse reflection image 116. The rate of the specular reflection image 117 to be added may be set in advance or arbitrarily determined by a user as gloss. Although the gloss of the image may be controlled using the diffuse reflection image 116 and the specular reflection image 117, the gloss may be controlled by the weighting subtraction which changes the rate of the specular reflection image 117 to be subtracted from the input image 110.

As described above, according to this embodiment, the diffuse reflection components may be estimated with high accuracy from an input image by reducing influence of noise.

Second Embodiment

In this embodiment, a method for obtaining a second hue by a noise reduction process performed based on a tentative specular reflection image which is specular reflection components of an input image so that diffuse reflection components are estimated from the input image will be described.

Figure 7:
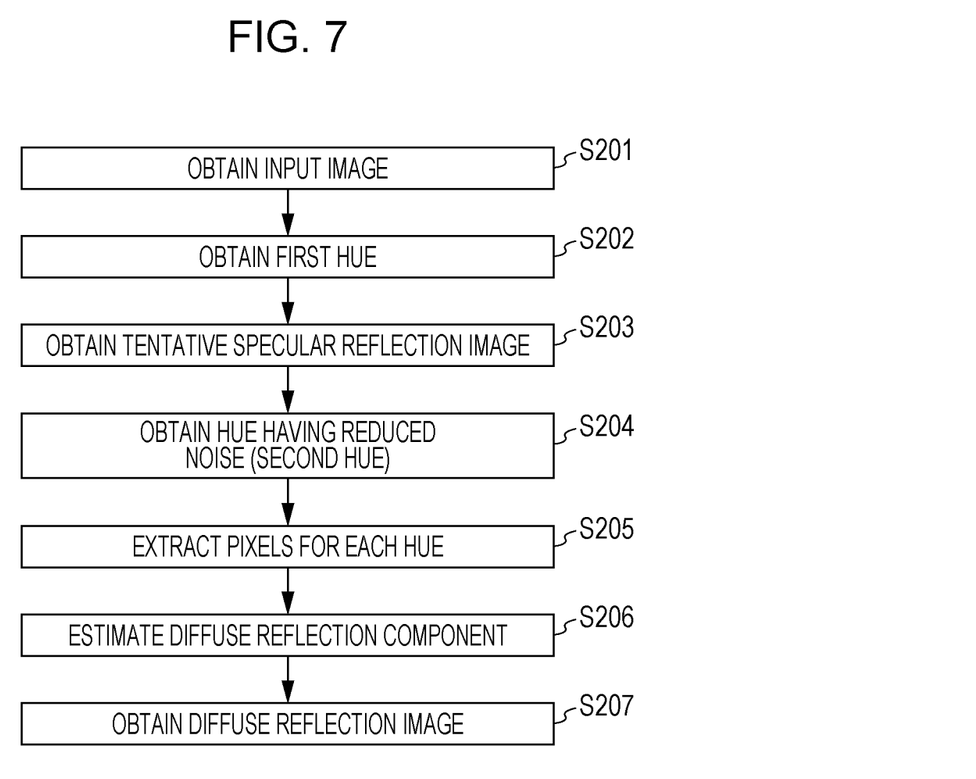
FIG. 7 is a flowchart of an image processing method according to the second embodiment.
Figure 8:
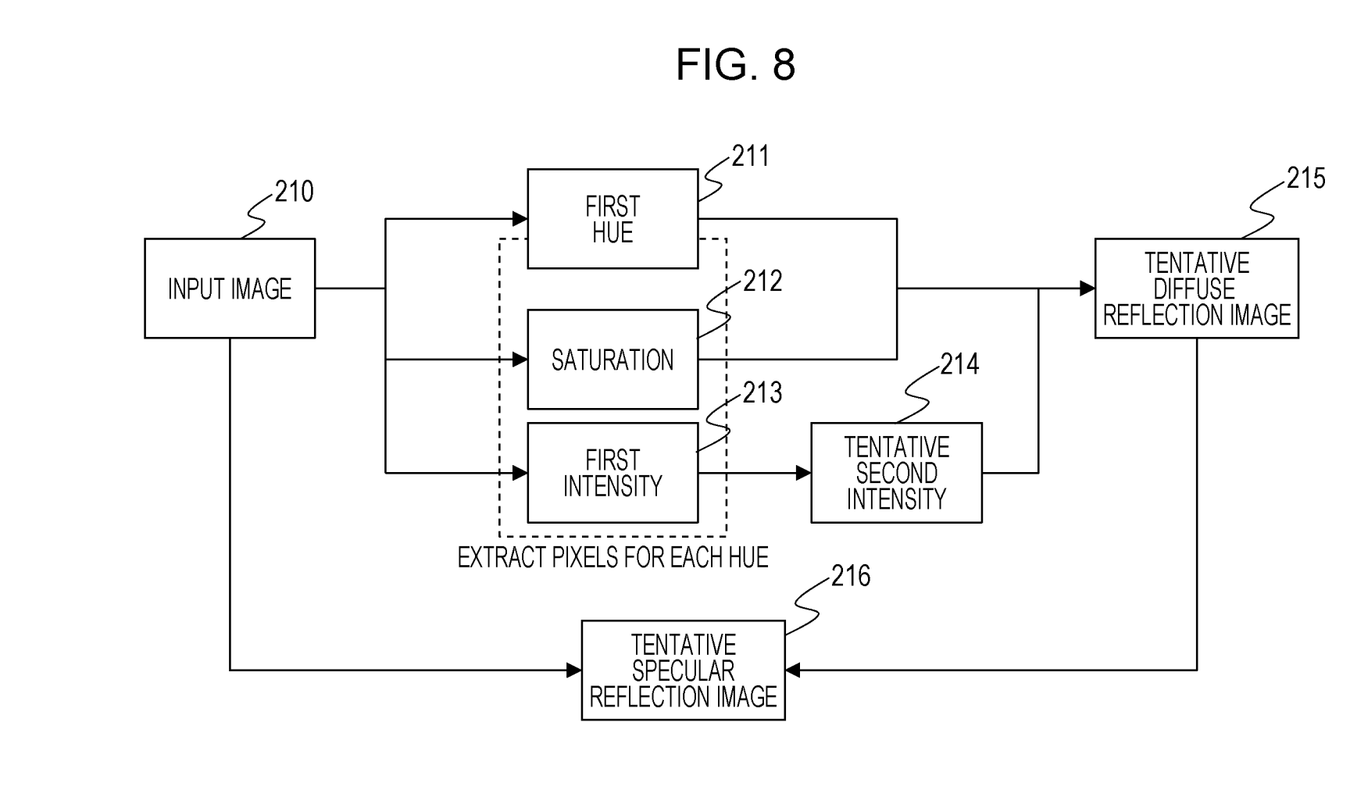
FIG. 8 is a diagram schematically illustrating a flow of obtainment of a tentative specular reflection image by the image processing method according to the second embodiment.

FIG. 7 is a flowchart of an image processing method according to this embodiment, and FIG. 8 is a diagram schematically illustrating a flow (step S201 to step S203) of obtainment of a tentative specular reflection image used in this embodiment. The image processing method of this embodiment is executed in accordance with an image processing program serving as a computer program by the system controller 109 and the image processor 104. Note that the image processing program may be recorded in a computer-readable recording medium, for example. Since a process in step S201 and a process in step S205 to step S207 are the same as the process in step S101 and the process in step S103 to step S105 according to the first embodiment, detailed descriptions thereof are omitted.

In step S202, a hue obtaining unit 104b obtains hue (a first hue 211) in an input image 210. The hue is calculated in accordance with Expressions (1) and (2) similarly to the first embodiment.

Subsequently, in step S203, the hue obtaining unit 104b obtains (generates) a tentative specular reflection image 216 which is specular reflection components included in the input image 210. The tentative specular reflection image 216 may be obtained (generated) by subtracting a tentative diffuse reflection image 215 from the input image 210 after the tentative diffuse reflection image 215 is obtained (generated) in a flow similar to the flow in step S103 to step S105 according to the first embodiment based on the first hue 211.

Next, in step S204, the hue obtaining unit 104b obtains hue (a second hue) having reduced noise based on the tentative specular reflection image 216 obtained in step S203. A specular reflection region 118 in the input image has a luminance value higher than that of the diffuse reflection region and brightness lower than that of the diffuse reflection region, and therefore, variation in hue is large due to noise. Accordingly, as a region has larger specular reflection, a degree of the noise reduction process is increased. Here, the tentative diffuse reflection image 215 obtained based on the first hue 211 is used as the tentative specular reflection image 216 obtained in step S203, and estimation accuracy is low due to influence of noise. Accordingly, an image obtained by performing a smoothing process on the tentative specular reflection image 216 may be used.

As with the first embodiment, a second hue in an image obtained by performing a noise reduction process on the input image may be obtained or a second hue may be obtained by performing the noise reduction process on hue (a first hue) of the input image in this embodiment.

In step S205 to step S207, as with the first embodiment, a diffuse reflection image is obtained (generated) using the second hue. Since the second hue having noise reduced based on the tentative specular reflection image 216 is used in this embodiment, diffuse reflection components may be estimated with high accuracy from the input image while influence of noise is reduced.

Although the preferred embodiments of the present disclosure have been described above, the present invention is not limited to these embodiments, and various modifications and changes may be made within the scope of the invention.

According to the present disclosure, an image processing apparatus, an imaging apparatus, an image processing method, an image processing program, and a recording medium which may estimate diffuse reflection components in an input image with high accuracy by reducing influence of noise may be provided.

While the present disclosure has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of International Patent Application No. PCT/JP2016/085511, filed Nov. 30, 2016, which is hereby incorporated by reference herein in its entirety.

The invention claimed is:

1. An image processing apparatus comprising:
a processor that executes a plurality of tasks, the plurality of tasks including:
a hue obtaining task that performs a noise reduction process on an input image or a first hue of the input image so as to obtain a second hue of the input image having reduced noise;
an extraction task that extracts a plurality of pixels from the input image based on the second hue having the reduced noise;
an estimation task that estimates, based on saturation and first intensity of the plurality of pixels extracted by the extraction task, second intensity of diffuse reflection components of the input image; and
an image generation task that generates a diffuse reflection image using the saturation, the second intensity and one of the first hue and the second hue.

2. The image processing apparatus according to claim 1, wherein the hue obtaining task performs the noise reduction process on the input image so as to obtain the second hue.

3. The image processing apparatus according to claim 1, wherein the hue obtaining task performs the noise reduction process on the first hue of the input image so as to obtain the second hue.

4. The image processing apparatus according to claim 1, wherein the plurality of tasks further includes a gloss controlling task that obtains a specular reflection image based on the diffuse reflection image and the input image.

5. The image processing apparatus according to claim 4, wherein the gloss controlling task performs gloss control of an image by performing weighting addition between the diffuse reflection image and the specular reflection image.

6. The image processing apparatus according to claim 4, wherein the gloss controlling task performs gloss control on the image by weighting subtraction between the input image and the specular reflection image.

7. The image processing apparatus according to claim 1, wherein the noise reduction process is performed based on a tentative specular reflection image which corresponds to specular reflection components of the input image.

8. The image processing apparatus according to claim 7, wherein the tentative specular reflection image is estimated based on the tentative diffuse reflection image estimated based on the plurality of pixels extracted from the input image based on the first hue.

9. The image processing apparatus according to claim 1, wherein the noise reduction process is performed based on brightness of color of the input image.

10. The image processing apparatus according to claim 9, wherein a degree of the noise reduction process is increased as the brightness of color of the input image is lowered.

11. The image processing apparatus according to claim 1, wherein the noise reduction process is performed based on a noise amount in the input image.

12. The image processing apparatus according to claim 11, wherein the noise amount is determined based on an ISO speed at a time of imaging and a luminance value of the input image.

13. An imaging apparatus comprising:
an imaging element that captures an image of an object; and
a processor that executes a plurality of tasks, the plurality of tasks including:
a hue obtaining task that performs a noise reduction process on an input image or a first hue of the input image so as to obtain a second hue of the input image having reduced noise;
an extraction task that extracts a plurality of pixels from the input image based on the second hue having the reduced noise;
an estimation task that estimates, based on saturation and first intensity of the plurality of pixels extracted by the extraction task, second intensity of diffuse reflection components of the input image, and
an image generation task that generates a diffuse reflection image using the saturation, the second intensity and one of the first hue and the second hue.

14. An image processing method comprising:
obtaining a second hue of an input image having reduced noise by performing a noise reduction process on the input image or a first hue of the input image;
extracting a plurality of pixels from the input image based on the second hue;
estimating, based on saturation and first intensity of the plurality of extracted pixels, second intensity of diffuse reflection components of the input image; and
generating a diffuse reflection image using the saturation, the second intensity and one of the first hue and the second hue.

15. A computer readable recording medium recording at least one program that causes a processor to execute an image processing method according to claim 14.

* * * * *